(12) United States Patent
Da Rold et al.

(10) Patent No.: US 6,592,256 B2
(45) Date of Patent: Jul. 15, 2003

(54) FILM HOLDER FOR DENTAL TECHNIQUE

(75) Inventors: Marc Da Rold, Vaglio (CH); Beat Kilcher, Bosco Luganese (CH); Rolf M. Klauser, Kriens (CH)

(73) Assignee: Hawe Neos Dental SA (CH)

( * ) Notice: Subject to any disclaimer, the term of this patent is extended or adjusted under 35 U.S.C. 154(b) by 0 days.

(21) Appl. No.: 10/142,207

(22) Filed: May 9, 2002

(65) Prior Publication Data

US 2002/0176539 A1 Nov. 28, 2002

(51) Int. Cl.[7] .................................. G03B 42/02
(52) U.S. Cl. ........................ 378/168; 378/191
(58) Field of Search .................. 378/168–170, 378/191

(56) References Cited

U.S. PATENT DOCUMENTS 4,592,084 A   5/1986   McAuslan ............. 378/170
5,022,065 A   6/1991   Wijkstrom ............. 378/168
5,737,388 A   4/1998   Kossila ................. 378/168

FOREIGN PATENT DOCUMENTS

GB   1043495   3/1965

*Primary Examiner*—Craig E. Church
(74) *Attorney, Agent, or Firm*—Wood, Herron & Evans LLP

(57) ABSTRACT

The film holder for dental technique comprises a bite portion (4) and an approximately U-shaped film clip (5) including an oral (6) and a facial (7) plate. For a safe retention also of thin digital picture plates or of films and picture plates having an uneven topography without damaging their sensitive surfaces, the facial plate (7) is provided with means allowing to obtain a pressure distribution adapted to different thicknesses and/or topographies of films or digital picture plates.

4 Claims, 1 Drawing Sheet

FILM HOLDER FOR DENTAL TECHNIQUE

FIELD OF THE INVENTION

The present invention refers to a film holder for dental technique, comprising a bite portion and an approximately U-shaped film clip. A film holder of this kind is described in European Patent No. 0,397,599. The film holder described in this reference, which has been on the market for a long time, is an X-ray film holder that includes a pointer device, inter alia. The X-ray film holder of the prior art comprises a U-shaped film clip including a back plate as well as a clamping shank, the dimensions of the back plate exactly corresponding to film format no. 0.

BACKGROUND OF THE INVENTION

The U-shaped configuration of the film clip is disadvantageous in that a clamping action on the entire film surface is only achieved in one ideal case, namely when the thickness of the film conforms to the angle of curvature of the U-shaped junction of the two shanks and to the mutual distance of the shanks. Lately, the conventional, relatively thick X-ray films have increasingly been replaced by digital picture plates. The latter consist of a very thin carrier material provided with a radiation-sensitive storage layer. These digital picture plates are not only very then, but they also have a very smooth surface. Moreover, the surface may not be exposed to mechanical irritations or injuries that might cause erroneous signals in the scanner and the computer and thereby result in a faulty image on the monitor and in incorrect information.

SUMMARY OF THE INVENTION

On the background of this prior art, the object of the present invention is to provide a film holder whose film clip takes in account not only the inequal thickness of films and of digital picture plates, but also of possibly existing variations in thickness and border beads as well as of the particular properties of digital picture plates, so as to ensure a sufficiently firm retention for keeping the plates in place when introducing and positioning them inside the patient's mouth without damaging them.

This object is attained with a film holder wherein the film clip comprises an oral and a facial plate, the oral plate being more rigid than the facial plate, and the facial plate being designed such as to obtain a pressure distribution adapted to different thicknesses and/or topographies of films or digital picture plates. Further embodiments are described in the dependent claims.

BRIEF DESCRIPTION OF THE DRAWINGS

The invention will be explained in more detail hereinafter with reference to drawings of an exemplary embodiment.

DETAILED DESCRIPTION OF THE INVENTION

Figure 1:
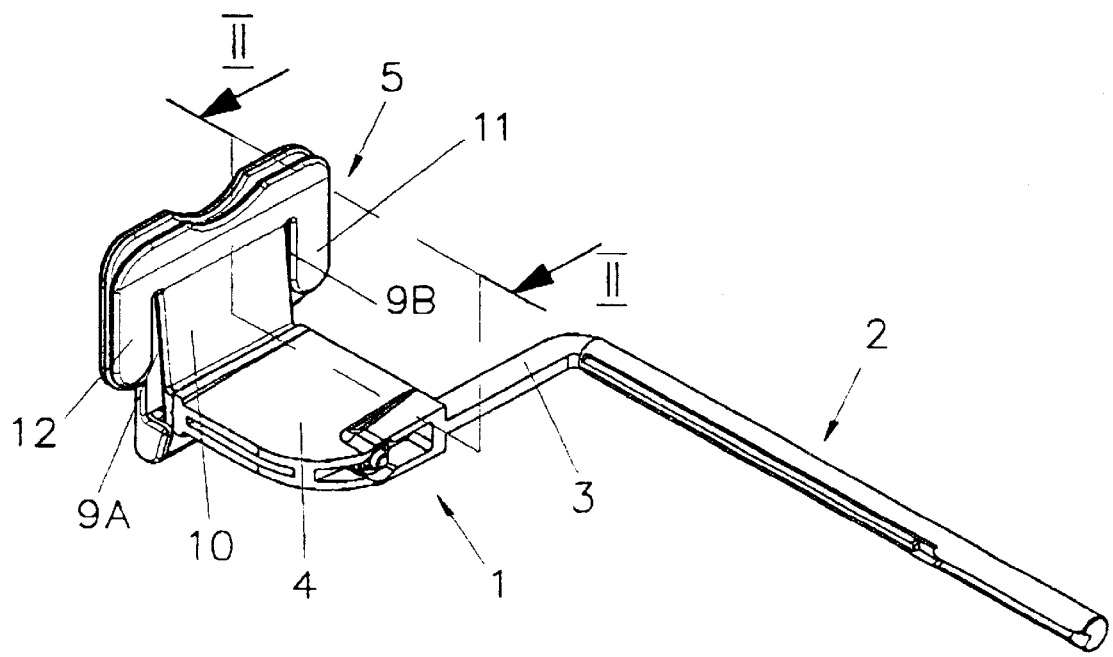
FIG. 1 shows the film holder of the invention in a perspective view.

FIG. 1 illustrates the essential parts of film holder which are known per se, i.e. indicator rod 2 with cranked portion 3 and, perpendicular to the latter, bite portion 4 with adjacent film clip 5. The indicator rod may hold different pointer devices, e.g. according to EP-patent No. 0,397,599 mentioned in the introduction, or according to Swiss patent No. 690,868.

Figure 2:
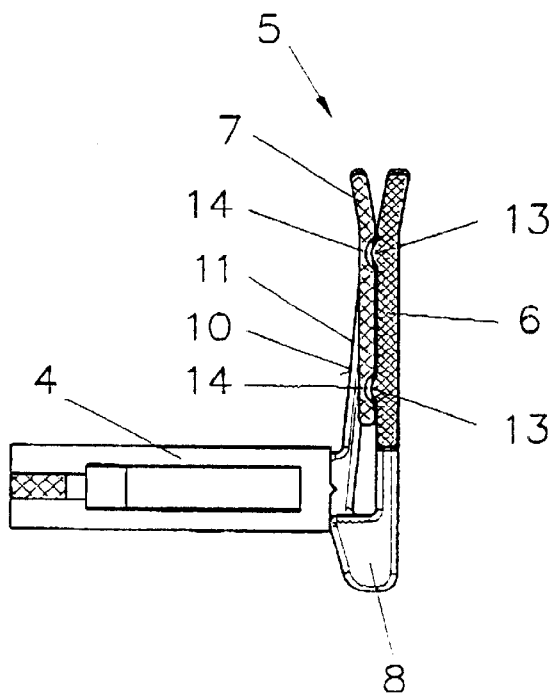
FIG. 2 shows a sectional view according to II/II in FIG. 1.

Film clip 5 is composed, see also FIG. 2, of a rearward oral film plate 6 and of a forward, facial film plate 7, which are connected to each other by a junction 8 resulting from the assembly of the oral and facial film plates. The width of the junction is chosen such that the film or the picture plate is not clamped at the junction itself. Rearward film plate 6 is thicker and also more rigid than forward plate 7, and generally consists of a single piece. Forward plate 7 is divided into sections each of which may be provided with a predetermined resilience due to the fact that the lower shank portions of lateral sections 11 and 12 do not lie in exactly the same plane as middle section 10, so that the pressure is not simply a result of the thickness of the film inserted in the film clip but distributed over several sections rather than being concentrated on a point or an edge only.

At the bottom, i.e. on the side of the bite portion, thinner forward plate 7 is provided with two incisions 9A and 9B dividing forward plate 7 into a middle section 10 and two lateral sections 11 and 12. The resulting facial plate 7 is thus divided into several sections and is therefore capable of adapting to different films, more particularly to the thin picture plates in such a manner that the pressure is distributed over the entire surface thereof. Instead of three sections, the forward plate may as well be divided into two or more than tree sections which are movable individually in order to be able to adapt to the thickness and the topography of the film or the picture plate. These sections may also be separated from each other by other means than incisions resp. vertical incisions.

In order to achieve a better clamping effect, oral plate 6 is provided with knobs 13 which cooperate with corresponding recesses 14 in the facial plate. In the present embodiment, four knobs 13 and recesses 14 are illustrated, but it is understood that there may be less, e.g. two or three, especially in smaller film clips, or more of them.

As already mentioned in the introduction, the clamping effect may be determined and pre-adjusted by using a suitable plastic material and by the choice of the wall thickness of the plates and of junction 8 in such a manner that picture plates are not damaged.

What we claim is:

1. A film holder for dental technique, comprising a bite portion and an approximately U-shaped film clip, wherein said film clip comprises an oral and a facial plate, the oral plate being more rigid than the facial plate, and the facial plate being designed such as to obtain a pressure distribution adapted to different thicknesses and/or topographies of films or digital picture plates.

2. The film holder of claim 1, wherein said facial plate is divided into sections, and wherein the lower shank portions of the lateral sections do not lie in exactly the same plane as the middle section.

3. The film holder of claim 1, wherein the inner sides of said film clamping plates are provided with knobs and corresponding recesses, respectively.

4. The film holder of claim 1, comprising an indicator rod with a cranked portion.

* * * * *